US009234202B2

(12) United States Patent
Cerchia et al.

(10) Patent No.: US 9,234,202 B2
(45) Date of Patent: Jan. 12, 2016

(54) NEUTRALIZING RNA APTAMERS

(71) Applicant: CONSIGLIO NAZIONALE DELLE RICERCHE, Rome (IT)

(72) Inventors: Laura Cerchia, Naples (IT); Gerolama Condorelli, Naples (IT); Vittorio De Franciscis, Naples (IT)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 0 days.

(21) Appl. No.: 14/433,386

(22) PCT Filed: Oct. 4, 2013

(86) PCT No.: PCT/EP2013/070724
§ 371 (c)(1),
(2) Date: Apr. 3, 2015

(87) PCT Pub. No.: WO2014/053640
PCT Pub. Date: Apr. 10, 2014

(65) Prior Publication Data
US 2015/0275215 A1   Oct. 1, 2015

(30) Foreign Application Priority Data

Oct. 5, 2012   (EP) .................................... 12187483

(51) Int. Cl.
*C12N 15/115*   (2010.01)
(52) U.S. Cl.
CPC .......... *C12N 15/115* (2013.01); *C12N 2310/16* (2013.01); *C12N 2310/3533* (2013.01)
(58) Field of Classification Search
CPC .................................................. C12N 15/115
See application file for complete search history.

(56) References Cited

U.S. PATENT DOCUMENTS

2012/0171304 A1   7/2012   Grate et al.

FOREIGN PATENT DOCUMENTS

| EP | 2159286 A1 | 3/2010 |
| EP | 2436391 A2 | 4/2012 |
| WO | 2006050498 A2 | 5/2006 |
| WO | 2010023327 A2 | 3/2010 |
| WO | 2012049108 A1 | 4/2012 |

OTHER PUBLICATIONS

Yucui Dong, Limin Jia, Xiaohua Wang, Xiaoqing Tan, Jiankai Xu, Zhenling Deng, Tao Jiang, Nikolai G. Rainov, Baoxin Li, Huan Ren, Selective inhibition of PDGFR by imatinib elicits the sustained activation of ERK and downstream receptor signaling in malignant glioma cells, International Journal of Oncology, 2011, pp. 555-569,vol. 38, Harbin Medical University, China, DOI:10.2892/ijo.2010.861.

Daniel George, Targeting PDGF receptors in cancer-rationales and proof of concept clinical trials, New Trends in Cancer for the 21st Century, 2003, pp. 141-151, Llombart-Bosch and Felipo, Kluwer Academic/Plenum Publishers, Boston, USA.

Jiuhong Yu, Carolyn Ustach and Hyeong-Reh Choi Kim, Platelet-derived Growth Factor Signaling and Human Cancer, Journal of Biochemistry and Molecular Biology, Jan. 2003, pp. 49-59, vol. 36, No. 1, KSBMB & Springer-Verlag, USA.

Y. Yarden, J. A. Escobedo, W-J. Kuang, T. L. Yang-Feng, T. O. Daniel, P.M. Tremble, E. Y. Chen, M. E. Ando, R. N. Harkins, U. Francke, V. A. Fried, A. Ullrich & L. T. Williams, Structure of the receptor for platelet-derived growth factor helps define a family of closely related growth factor receptors, Nature, Sep. 18, 1986, pp. 226-232, vol. 323, Nature Publishing Group, USA.

Flemming S. Vassbotn, Maria Andersson, Bengt Westermark, Carl-Henrik Heldin and Arne Östman, Reversion of Autocrine Transformation by a Dominant Negative Platelet-Derived Growth Factor Mutant, Molecular and Cellular Biology, Jul. 1993, pp. 4066-4076, vol. 13, No. 7, American Society for Microbiology, Norway and Sweden.

Carolyn V. Ustach, Wei Huang, M. Katie Conley-Lacomb, Chen-Yong Lin, Mingxin Che, Judith Abrams, Hyeong-Reh Choi Kim, A novel signaling axis of matriptase/PDGF-D/β-PDGFR in human prostate cancer, NIH Public Access, Cancer Res, Author Manuscript, Dec. 1, 2010, pp. 9631-9640, vol. 70 (23), doi: 10.1158/0008-5472.CAN-10-0511, USA.

Steven M. Shamah, Charles D. Stiles and Abhijit Guha, Dominant-Negative Mutants of Platelet-Derived Growth Factor Revert the Transformed Phenotype of Human Astrocytoma Cells, Molecular and Cellular Biology, Dec. 1993, pp. 7203-7212, vol. 13, No. 12, American Society for Microbiology, USA and Canada.

Vinochani Pillay, Layal Allaf, Alexander L. Wilding, Jacqui F. Donoghue, Naomi W. Court, Steve A. Greenall, Andrew M. Scott and Terrance G. Johns, The Plasticity of Oncogene Addiction: Implications for Targeted Therapies Directed to receptor Tyrosine Kinases, May 2009, pp. 448-458, vol. 11, No. 5, www.neoplasia.com, Australia.

Toshimitsu Matsui, Mohammad Heidaran, Toru Miki, Nicholas Popescu, William La Rochelle, Matthias Kraus, Jacalyn Pierce, Stuart Aaronson, Isolation of a Novel receptor cDNA Establishes the Existence of Two PDGF Receptor Genes, Science, www.sciencemag.org, Mar. 30, 2015, pp. 800-804, vol. 243.

(Continued)

*Primary Examiner* — Jon E Angell

(74) *Attorney, Agent, or Firm* — Robert E. Alderson, Jr.

(57) ABSTRACT

Nuclease-resistant RNA aptamers are provided which are capable of neutralizing PDGFRβ and are therefore useful in the diagnosis and/or therapy of PDGFRβ-associated and hyperproliferative-associated diseases, such as cancer and primary tumor metastasis. RNA aptamers provided herein include a modified synthetic RNA sequence wherein at least one pyrimidine residue is modified to 2'-fluoropyrimidine. Pharmaceutical compositions and diagnostic kits comprising RNA aptamers are also provided.

12 Claims, 13 Drawing Sheets

(56) References Cited

OTHER PUBLICATIONS

Turker Kilic, John A. Alberta, Pawel R. Zdunek, Melih Acar, Palma Iannarelli, Terence O'Reilly, Elisabeth Buchdunger, Peter M. Black, and Charles D. Stiles, Intracranial Inhibition of Platelet-derived Growth Factor-mediated Glioblastoma Cell Growth by an Orally Active Kinase Inhibitor of the 2-Phenylaminopyrimidine Class, Cancer research, cancerres.aacrjournals.org, Sep. 15, 2000, pp. 5143-5150, No. 60, American Association for Cancer Research, USA and Switzerland.

Renée V. Hoch and Philippe Soriano, Roles of PDGF in animal development, Development, 2003, pp. 4769-4784, No. 130, The Company of Biologists LTD, DOI: 10.1242/dev.00721, USA.

Richard J. Gilbertson, Steven C. Clifford, PDGFRB is overexpressed in metastatic medulloblastoma, Nature Genetics, www.nature.com/naturegenetics, Nov. 2003, pp. 197-198, vol. 35, No. 3, Nature Publishing Group.

Laura Cerchia, Jörg Hamm, Domenico Libri, Bertrand Tavitian, Vittorio De Franciscis, Nucleic acid aptamers in cancer medicine, FEBS Letters, 2002, pp. 12-16, No. 528, 26501, Federation of European Biochemical Societies, Elsevier Science B. V., Italy and France.

Laura Cerchia, Carla L Esposito, Simona Camorani, Anna Rienzo, Loredana Stasio, Luigi Insabato, Andrea Affuso, Vittorio De Franciscis, Targeting Axl with an high-affinity Inhibitory Aptamer, Molecular Therapy, Dec. 2012, pp. 2291-2303, vol. 20, No. 12, The American Society of Gene & Cell Therapy, Italy.

Laura Cerchia, Carla Lucia Esposito, Andreas H. Jacobs, Bertrand Tavitian, Vittorio De Franciscis, Differential Selex in Human Glioma Cell Lines, Plos One, www.plosone.org, Nov. 2009, pp. 1-10, vol. 4, Issue 11, e7971.

Laura Cerchia, Vittorio De Franciscis, Targeting cancer cells with nucleic acid aptamers, Cell Press, 2010, pp. 517-525, Trends in Biotechnology, vol. 28, No. 10, Elsevier Ltd., doi: 10.1016/j.tibtech.2010.07.005, Italy.

Renhai Cao, Meit A. Björndahl, Piotr Religa, Steve Clasper, Stina Garvin, Dagmar Galter, Björn Meister, Fumitaka Ikomi, Katerina Tritsaris, Steen Dissing, Toshio Ohhashi, David G. Jackson, Yihai Cao, PDGF-BB induces intratumoral lymphangiogenesis and promotes lymphatic metastasis, Cancer Cell: Oct. 2004, pp. 333-345, vol. 6, Cell press.

Christer Betsholtz, Linda Karlsson, Per Lindahl, Developmental roles of platelet-derived growth factors, BioEssays 23.6, 2001, pp. 494-507, BioEssays 23:494-507, John Wiley & Sons, Inc.

Johanna Andrae, Radiosa Gallini, Christer Betsholtz, Role of platelet-derived growth factors in physiology and medicine, Genes and Development 22:1276-1312, 2008, pp. 1276-1312, Cold Spring Harbor Laboratory Press ISSN 0890-9369/08; www.genesdev.org, Sweden.

Thamara J. Abouantoun, Tobey J. MacDonald, Imatinib blocks migration and invasion of medulloblastoma cells by concurrently inhibiting activation of platelet-derived growth factor receptor and transactivation of epidermal growth factor receptor, Molecular Cancer Therapeutics, May 5, 2009, pp. 1137-1147, DOI:10.1158/1535-7163. MCT-08-0889, American Association for Cancer Research.

A

*DNAsis software*

Gint4 aptamer    Gint4, 42-74 (33nt)

*RNA structure 4.5 software*

Gint4 aptamer    Gint4, 42-74 (33nt)

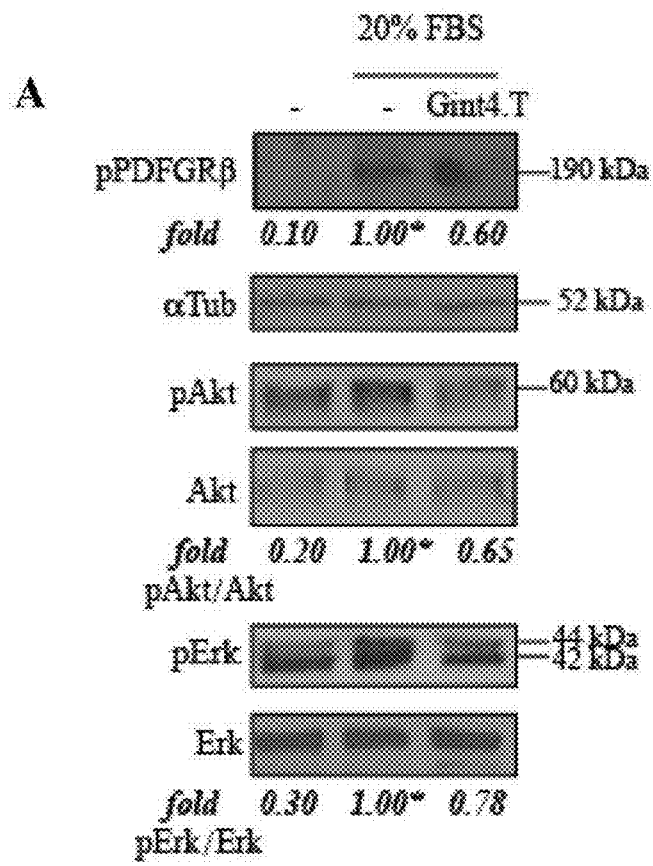
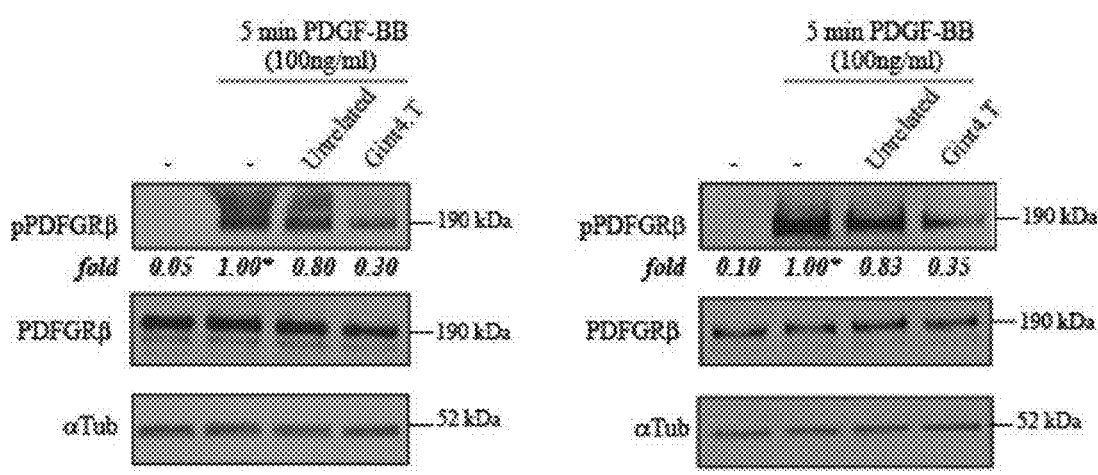
Fig. 5A
Fig. 5B
Fig. 5C

SEQUENCE LISTING

```
<160> NUMBER OF SEQ ID NOS: 2

<210> SEQ ID NO 1
<211> LENGTH: 33
<212> TYPE: RNA
<213> ORGANISM: Artificial
<220> FEATURE:
<223> OTHER INFORMATION: APTAMER

<400> SEQUENCE: 1
ugucgugggg caucgaguaa augcaauucg aca                              33

<210> SEQ ID NO 2
<211> LENGTH: 91
<212> TYPE: RNA
<213> ORGANISM: Artificial
<220> FEATURE:
<223> OTHER INFORMATION: APTAMER

<400> SEQUENCE: 2
gggagacaag aauaaacgcu caaucauaag agguaucaca uugucguggg gcaucgagua    60
aaugcaauuc gacaggaggc ucacaacagg c                                  91
```

NEUTRALIZING RNA APTAMERS

CROSS-REFERENCE TO RELATED APPLICATIONS

This application is a National Phase Application of PCT International Application No. PCT/EP2013/070724, International Filing Date, Oct. 4, 2013, claiming priority to European Patent Application No. 12187483.8, filed Oct. 5, 2012, each of which is hereby incorporated by reference in its entirety.

FIELD OF THE INVENTION

The present invention generally relates to the field of nucleic acids and more particularly to a modified RNA aptamer which is capable of binding to and inhibiting PDGFRβ. The RNA aptamer of the invention is useful in diagnostic, therapeutic and delivery applications, particularly in the field of cancer.

BACKGROUND OF THE INVENTION

Aptamers are single-stranded oligonucleotides which are able to bind with high affinity to specific protein or non-protein targets by folding into complex tertiary structures. Aptamers have generally proven useful as reagents for identifying cell surface proteins and for cell typing. Furthermore, their high specificity and low toxicity render them a valid alternative to antibodies for in vivo targeted recognition as therapeutics or delivery agents for nanoparticles, small interfering RNAs, chemotherapeutics and molecular imaging probes.

The platelet-derived growth factor receptor (PDGFR) is an important member of receptor tyrosine kinase (RTK) family. Its ligand, PDGF, has a wide array of important effects on mitogenesis, migration, and development.

More specifically, platelet-derived growth factors (PDGFs) are a family of potent mitogens for almost all mesenchyme-derived cells. The PDGF family consists of four polypeptides, A-D, forming five disulfide-linked dimeric proteins PDGF-AA, -BB, -AB, -CC, and -DD that signal through two structurally similar tyrosine kinase receptors, platelet-derived growth factor receptors α and β (PDGFRα and PDGFRβ). The ligands and receptors can form homodimers or heterodimers depending on cell type, receptor expression, and ligand availability. PDGF-BB and PDGF-DD are the primary activators of ββ homodimeric receptors. PDGF-AA activates only αα receptor dimers, whereas PDGF-AB, PDGF-BB, and PDGF-CC activate αα and αβ receptor dimers (Yarden Y et al., 1986; Matsui T et al., 1989). PDGF receptors have been extensively studied regarding their signaling mechanism, in particular PDGFRβ. The dimeric ligand molecules bind to two receptor proteins simultaneously and induce receptor dimerization, autophosphorylation of specific residues within the receptor's cytoplasmic domain, and intracellular signaling. It has been demonstrated that the activation of PDGFRβ signaling pathway induces various cellular responses, including cell proliferation, migration and angiogenesis (Andrae et al., 2008; Ustach et al., 2010; Cao et al., 2004).

In embryogenesis the PDGFR/PDGF system is essential for the correct development of the kidney, cardiovascular system, brain, lung and connective tissue (Betsholtz et al., 2001; Hoch et al., 2003). In adults, it is important in wound healing, inflammation and angiogenesis. Abnormalities of PDGFR/PDGF are thought to contribute to a number of human diseases including cancer. Overexpression, point mutations, deletions and translocations of PDGFR, including PDGFRβ, have been described in many tumors (Gilbertson et al., 2003; Yu et al., 2003; George, 2003).

Furthermore, preclinical studies have not only shown an important role for the overexpression and deregulated activation of PDGFRβ-mediated signaling in tumorigenesis and the maintenance of the malignant phenotype, but have also proven that the targeted inhibition of signaling cascades has significant anti-cancer effects (Vassbotn et al., 1993; Kilic et al., 2000; Shamah et al., 1993). Overall these data indicate that PDGFRβ represents a valuable target for tumor therapeutic development (George, 2003).

A number of tyrosine kinase inhibitors under development as anti-tumor agents have been found to inhibit the PDGFRβ. However, these compounds are not selective and have multiple tyrosine kinase targets. Since these small molecule antagonists are not specific to this receptor, it is not possible to distinguish the contribution of PDGFRβ signaling to cancer, including tumor-associated angiogenesis, tumor stimulation and growth, or toxicities associated with administration of such compounds that might be due to unnecessary targeting of multiple receptors.

Among the small molecular inhibitors of PDGFR that act on a wide spectrum of tyrosine protein kinases, imatinib mesylate (Gleevec®/ST571) was developed as an Abelson (Abl) tyrosine kinase inhibitor, and also inhibits c-kit, PDGFRα, and PDGFRβ. Sunitinib malate (Sutent®/SU11248) is a broad-spectrum, orally available multitargeted tyrosine kinase inhibitor with activity against VEGFR, PDGFR, c-KIT, and FLT-3. CP-673,451 is an inhibitor of both PDGFRα and PDGFRβ. Sorafenib (Nexavar®) is an inhibitor of Ras/Raf/MEK/ERK pathway and of angiogenic RTKs VEGFR2 and PDGFRβ. However, toxicity is associated with administration of such compounds that might be due to unnecessary targeting of multiple receptors.

Neutralizing antibodies exist for PDGF ligands and receptors and have been used extensively in experiments evaluating the importance of PDGF signaling in pathogenic processes but, to date, no antibodies exist in clinic (Johanna et al., 2008).

Thus, there is the urgent need to provide a new PDGFRβ-targeting drug for a more specific and selective tumour therapy.

SUMMARY OF THE INVENTION

To meet these and other needs, the present invention provides novel PDGFRβ-specific aptamers which are disclosed and claimed herein.

This is the first report of an aptamer that inhibits PDGFRβ by directly binding to PDGF receptor RTK. Indeed, the aptamer named ARC126 (European patent application EP2436391) and different PEGylated and chemically modified derivative of AR126, bind to the ligand Platelet-derived growth factor-B (PDGF-B) and not to PDGF receptor. The aptamer blocked PDGF-B-induced proliferation by binding to ligand and not to its correspondent receptor.

BRIEF DESCRIPTION OF THE FIGURES

FIGS. 5A, 5B, 5C, 5D show that Gint4.T inhibits PDGFRβ activity. Values below the blots indicate signal levels relative to FBS and PDGF-BB stimulated controls.

DETAILED DESCRIPTION

Figure 1:
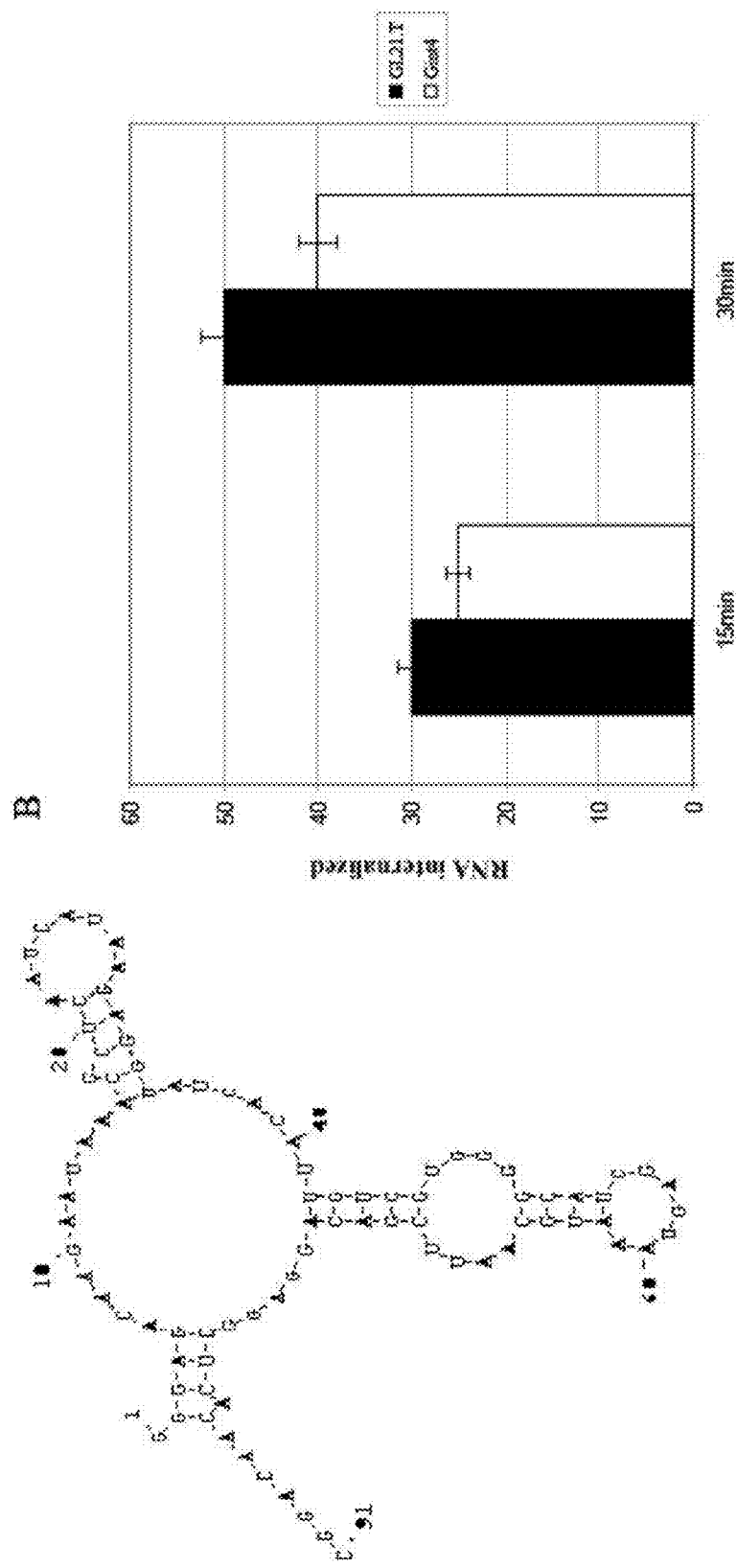
FIG. 1 shows (A) a nucleotide sequence of Gint4 aptamer and all the pyrimidines of the sequence are 2'F-Py. (B) internalization of Gint4 into U87MG cells.

The present inventors identified a synthetic RNA aptamer which is 91 bases in length, named as Gint4, which is capable of binding at high affinity and specificity and of inhibiting the human PDGF receptor β, and which is useful in diagnostic and therapeutic applications.

Moreover, the present inventors found that Gint4 rapidly and specifically internalizes within the target cells. Specifically, the inventors observed that Gint4 is rapidly endocytosed in glioma cells, reaching about 25% of cell internalization after 15 min incubation and about 40% of cell internalization after a 30 min treatment. Gint4 is therefore particularly suitable as a cargo for tissue specific internalization and drug delivery applications, such as the delivery of small cytotoxic molecules (such as small interfering RNAs) targeted to tumour sites.

The inventors further identified a 33mer truncated version of the Gint4 aptamer (named as Gint4.T), which contains the aptamer active site and retains the ability to bind at high affinity to PDGFRβ and to be rapidly internalized within the target cells.

It is therefore an aspect of the present invention a RNA aptamer which consists of or comprises the following nucleic acid sequence of 33 bases in length:

```
                                            (SEQ ID NO: 1)
   5' UGUCGUGGGGCAUCGAGUAAAUGCAAUUCGACA 3'.
```

According to a preferred embodiment, the RNA aptamer of the invention consists of the following nucleic acid sequence of 91 bases in length:

```
                                            (Seq ID NO: 2)
GGGAGACAAGAAUAAACGCUCAAUCAUAAGAGGUAUCACAUUGUCGUGGGG

CAUCGAGUAAAUGCAAUUCGACAGGAGGCUCACAACAGGC.
```

In another preferred embodiment of the invention, at least one of the pyrimidine residues of Gint4.T (SEQ ID NO:1) or Gint4 (SEQ ID NO:2) is modified to 2'-fluoropyrimidines. More preferably, all of the pyrimidine residues in SEQ ID NOs:1 and/or 2 are modified to 2'-fluoropyrimidines. In the present invention, the pyrimidine residues may alternatively be modified as 2'-O-alkyl nucleotides or 3' end cap and locked nucleic acids or as LNA modifications to significantly enhance RNA stability.

According to another preferred embodiment, the RNA aptamer of the present invention as described above is nuclease-resistant.

The RNA aptamer of the invention was generated by an in vitro evolution-based approach named as SELEX (Systematic Evolution of Ligands by EXponential enrichment) on highly tumorigenic malignant glioma target cells.

As it will be illustrated in more detail in the experimental section of the present patent description, the inventors found that the Gint4 aptamer of the invention, as well as the 33mer truncated form thereof (Gint4.T), are able to specifically bind to the extracellular domain of the human PDGFRβ and that, following binding, they hamper ligand-dependent receptor dimerization and autophosphorylation. Moreover, the treatment of tumour PDGFRβ-positive cells with the RNA aptamer of the invention strongly affects serum-induced PDGFRβ phosphorylation and activation of the intracellular pathways that are essential for cancer development and progression, i.e. the ERK pathway involved in cell proliferation and the pro-survival Akt pathway.

Thus, another aspect of the present invention is the Gint4 aptamer or Gint4.T truncated form thereof as defined above for use in a method of diagnosis and/or therapy of a hyperproliferative disease, particularly a PDGFRβ-associated hyperproliferative disease, as well as the use of the Gint4 aptamer Gint4.T truncated form thereof in drug delivery applications.

The hyperproliferative disease is preferably selected from cancer and primary tumour metastasis, such as for example gastrointestinal cancer, prostate cancer, ovarian cancer, breast cancer, head and neck cancer, lung cancer, non-small cell lung cancer, cancer of the nervous system (i.e. glioma), kidney cancer, retina cancer, skin cancer, liver cancer, pancreatic cancer, genital-urinary cancer, bladder cancer as well as metastasis thereof.

A further aspect of the present invention is a pharmaceutical composition comprising the RNA aptamer Gint4 or Gint4.T as defined above, preferably for use in a method of diagnosis or therapy of a hyperproliferative disease as defined above. In a preferred embodiment, the pharmaceutical composition also comprises pharmaceutically acceptable carrier(s), diluent(s) and/or excipients. The selection and use of suitable pharmaceutically acceptable carrier(s), diluent(s) and/or excipients is comprised within the abilities of the skilled in the art.

Yet another aspect of the invention is a kit for the diagnosis of a disease as defined above, which comprises the RNA aptamer Gint4 or Gint4.T according to the invention.

Yet a further aspect of the present invention is a method of inhibiting PDGF receptor β comprising administering to a subject an aptamer as defined above or a pharmaceutical composition comprising the aptamer as defined above. The method is particularly suitable for the treatment of a hyperproliferative disease, such as cancer or primary tumour metastasis, preferably a gastrointestinal cancer, prostate cancer, ovarian cancer, breast cancer, head and neck cancer, lung cancer, non-small cell lung cancer, cancer of the nervous system (i.e. glioma), kidney cancer, retina cancer, skin cancer, liver cancer, pancreatic cancer, genital-urinary cancer, bladder cancer or metastasis thereof.

The following experimental section has the purpose of illustrating the invention in further detail without limiting the scope thereof.

FIG. 1. Gint4 aptamer. (A) Nucleotide sequence of Gint4 aptamer. All the pyrimidines of the sequence are 2'F-Py. Secondary structure of Gint4 Full Length predicted by using DNAsis software. (B) Internalization of Gint4 into U87MG cells. Gint4 aptamer has been 5' $^{32}$P-labelled and incubated on U87MG cells. At the indicated times, cells have been treated with proteinase K and the amount of RNA internalised has been recovered and counted. % of internalization has been obtained by subtracting the unspecific counts relative to the unrelated aptamer used as a negative control. In the experiment, GL21.T (the anti-Axl aptamer) has been used as a positive control since it rapidly internalizes into target cells.

Figure 2A:
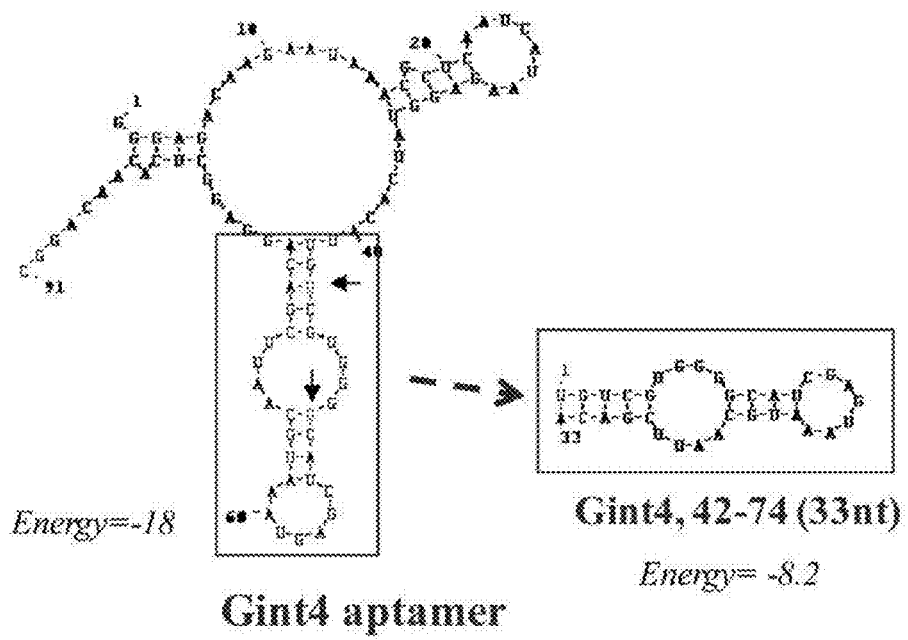
FIGS. 2A, 2B, 2C show that Gint4.T preserves high binding affinity to the U87MG cells and internalization rate. (A) Secondary structure of Gint.4 full Length and Gint4.T (nucleotides from 42 to 74, boxed). (B) Binding of Gint4.T aptamer on U87MG in comparison with the entire Gint4 sequence. (C) Internalization rate of Gint4.T and unrelated aptamer.
Figure 2A:
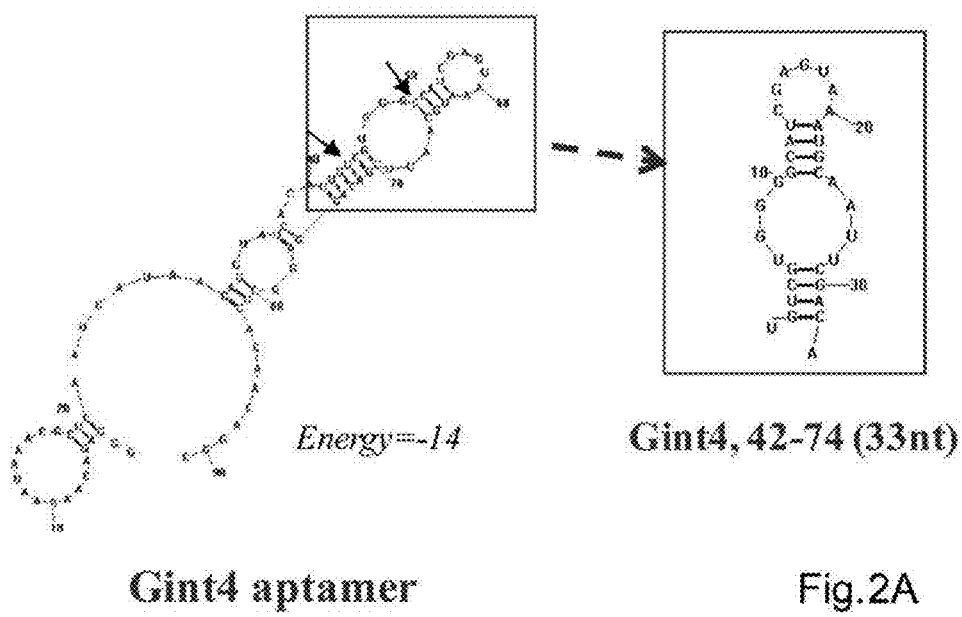
Figure 2B:
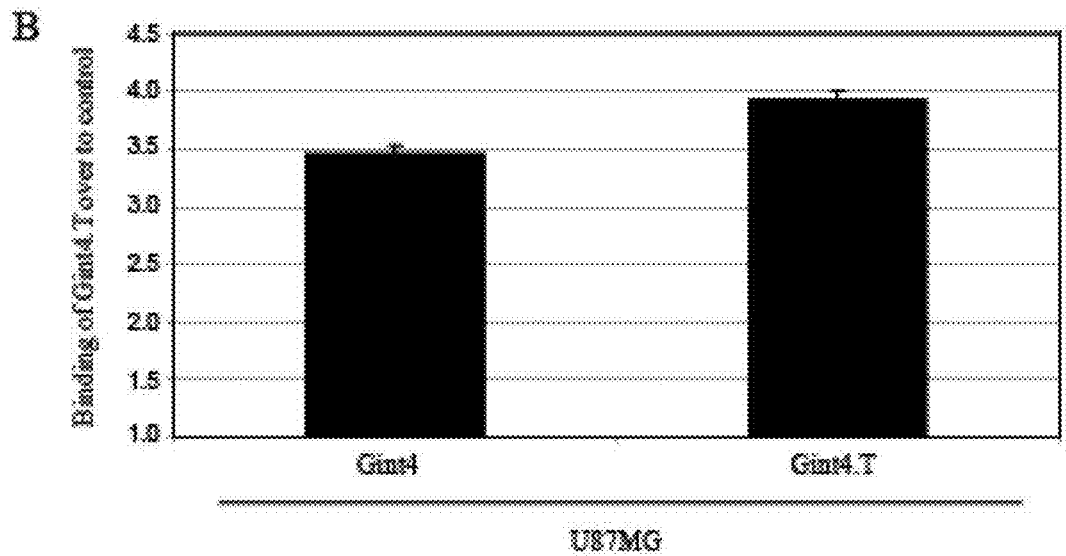
Figure 2C:
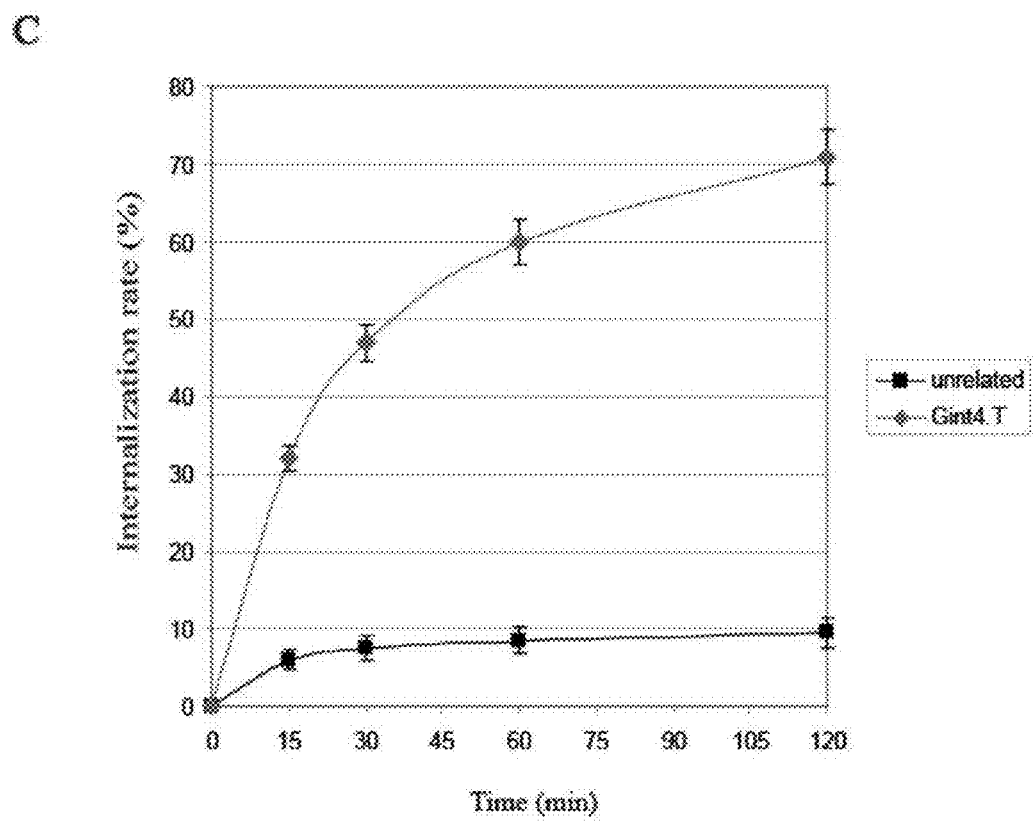

FIGS. 2A, 2B, 2C. Gint4.T preserves high binding affinity to the U87MG cells and internalization rate. (A) Secondary structure of Gint.4 full Length and Gint4.T (nucleotides from 42 to 74, boxed) predicted by using DNAsis software (left) and RNA structure 4.5 software (right). (B) Binding of Gint4.T aptamer on U87MG in comparison with the entire Gint4 sequence (100 nM radiolabeled aptamers, 15 min incubation). The results are expressed relative to the background binding detected with the unrelated aptamer used as a negative control. (C) Internalization rate of Gint4.T and unrelated aptamer. Results are expressed as percentage of internalized RNA relative to total bound aptamer. In (B,C), error bars depict means±SD (n=3).

Figure 3:
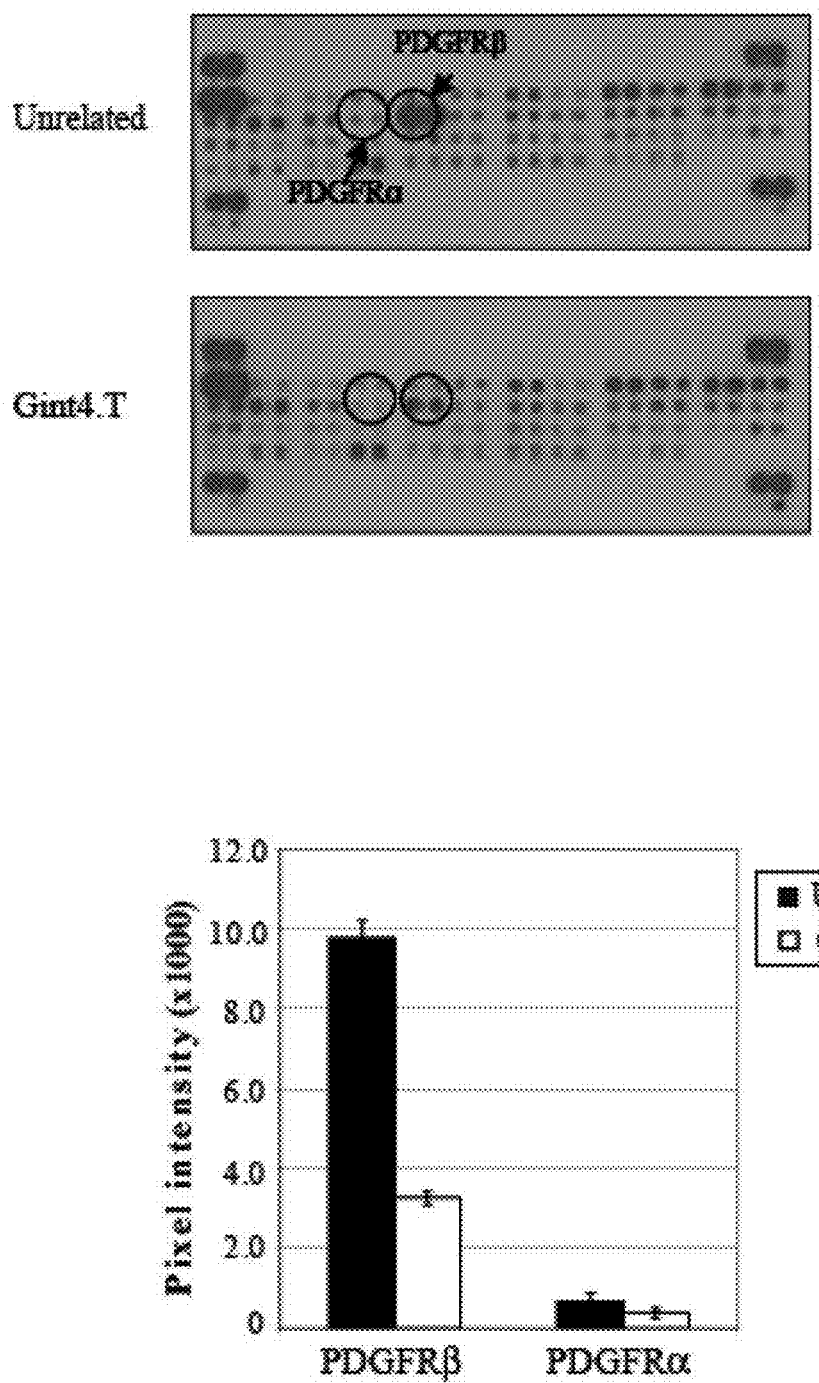
FIG. 3 shows Gint4.T target identification. Arrows indicate phospho-PDGFR levels.

FIG. 3. Gint4.T target identification. U87MG cells were serum starved overnight, treated for 3 h with 200 nM Gint4.T or unrelated aptamer and then stimulated with culture medium supplemented with 20% FBS for 10 min in the presence of 200 nM Gint4.T or unrelated aptamer. Cell extracts were prepared and 200 µg-lysates were incubated on RTK antibody arrays. Phosphorylation levels were determined by subsequent incubation with anti-phosphotyrosine horseradish peroxidase. Arrows indicate phospho-PDGFR levels. The pixel intensity associated to the phosphorylation status of PDGFRβ and α is reported. Error bars depict means±s.d. (n=4).

Figure 4A:
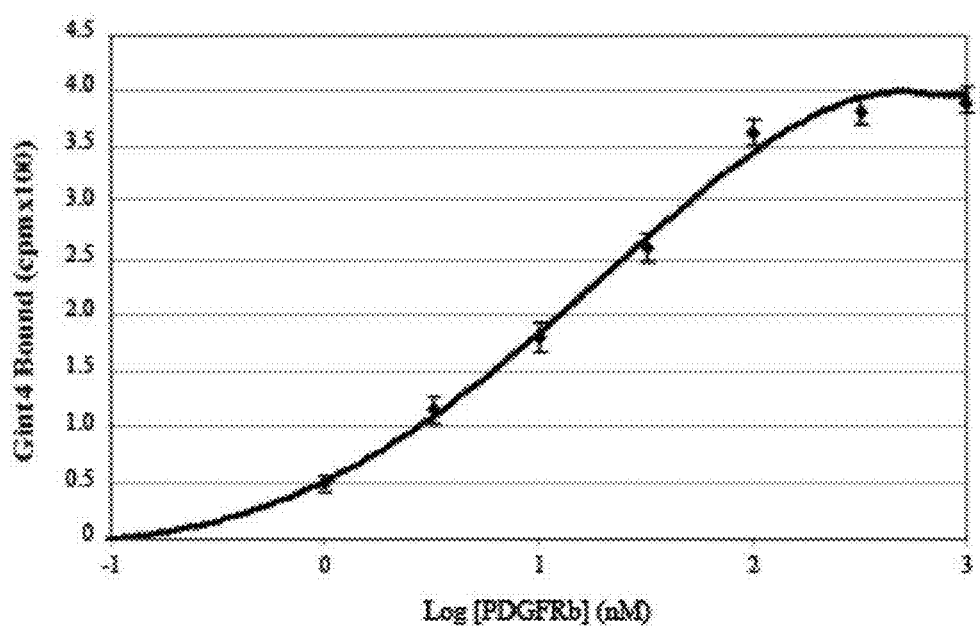
FIGS. 4A, 4B show that Gint4.T specifically binds PDGFRβ. (A) Binding isotherm for Gint4:PDGFRβ (upper panel) and Gint4.T:PDGFRβ (bottom panel) complexes. (B) Binding of 100 nM radiolabeled Gint4.T. In (A-B), the results are expressed relative to the background binding detected with unrelated aptamer used as a negative control.
Figure 4A:
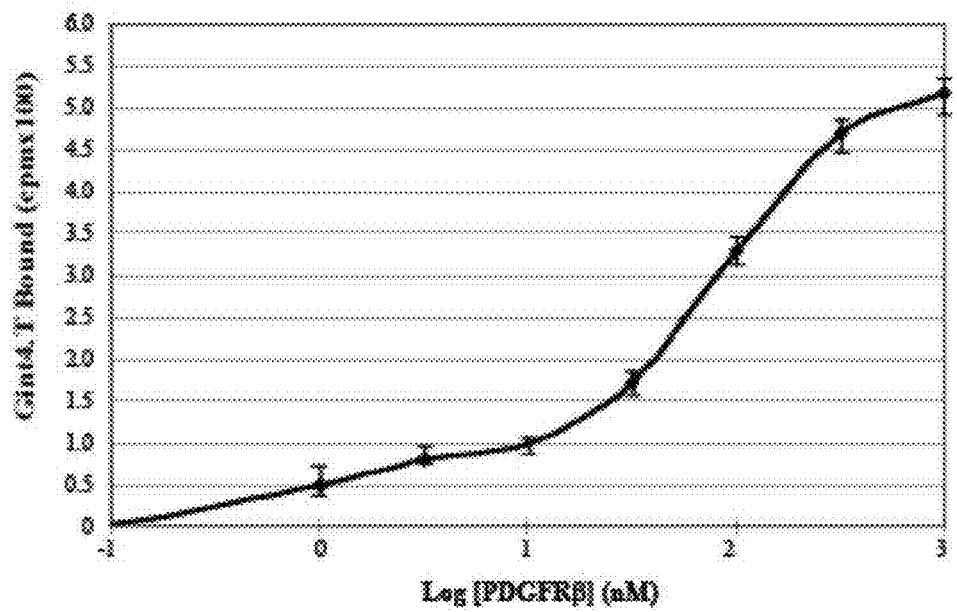
Figure 4B:
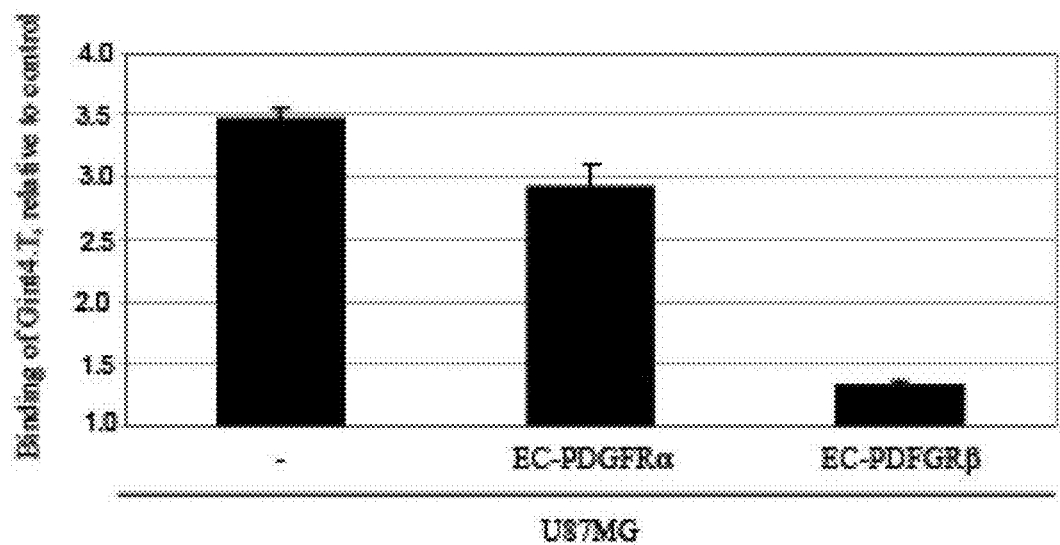

FIGS. 4A, 4B. Gint4.T specifically binds PDGFRβ. (A) Binding isotherm for Gint4:PDGFRβ (upper panel) and Gint4.T:PDGFRβ (bottom panel) complexes. Kd value was derived by fitting bound Gint4 and Gint4.T versus the protein concentration to the equation Y=BmaxX/(Kd+X), where Bmax is the extrapolated maximal amount of RNA:protein complex bound. (B) Binding of 100 nM radiolabeled Gint4.T, prior incubated with 200 nM EC-PDGFRα or EC-PDGFRβ for 15 min at 37° C., on U87MG cells. In (A-B), the results are expressed relative to the background binding detected with unrelated aptamer used as a negative control.

FIGS. 5A, 5B, 5C, 5D. Gint4.T inhibits PDGFRβ activity. (A) Serum starved U87MG cells (150,000 cells per 3.5-cm plate) were either left untreated or treated for 3 h with 200 nM Gint4.T and then stimulated for 10 min with 20% fetal bovine serum alone or in the presence of aptamer. Serum starved U87MG (B) and U87MGΔEGFR (C) (150,000 cells per 3.5-cm plate) were either left untreated or treated for 3 h with 200 nM Gint4.T or unrelated aptamer and then stimulated for 5 min with PDGF-BB (100 ng/ml) ligand alone or in the presence of each aptamer. (D) U87MG (150,000 cells per 3.5-cm plate) were treated for 3 h with 200 nM Gint4.T or unrelated aptamer and then stimulated for 5 min with PDGF-BB (100 ng/ml) ligand alone or in the presence of each aptamer. NS, not serum starved. Cell lysates were immunoblotted with anti-(phospho)-PDGFRβ (pPDGFRβ), anti-PDGFRβ antibodies, anti-(phospho)-ERK1/2 (pERK), anti-ERK1, anti-(phospho)-AKT (pAKT), anti-AKT antibodies, as indicated. In all experiments, αtubulin was used as an internal control of loading. Values below the blots indicate signal levels relative to FBS and PDGF-BB stimulated controls, arbitrarily set to 1 (labeled with asterisk). Molecular weights of indicated proteins are reported.

Figure 6:
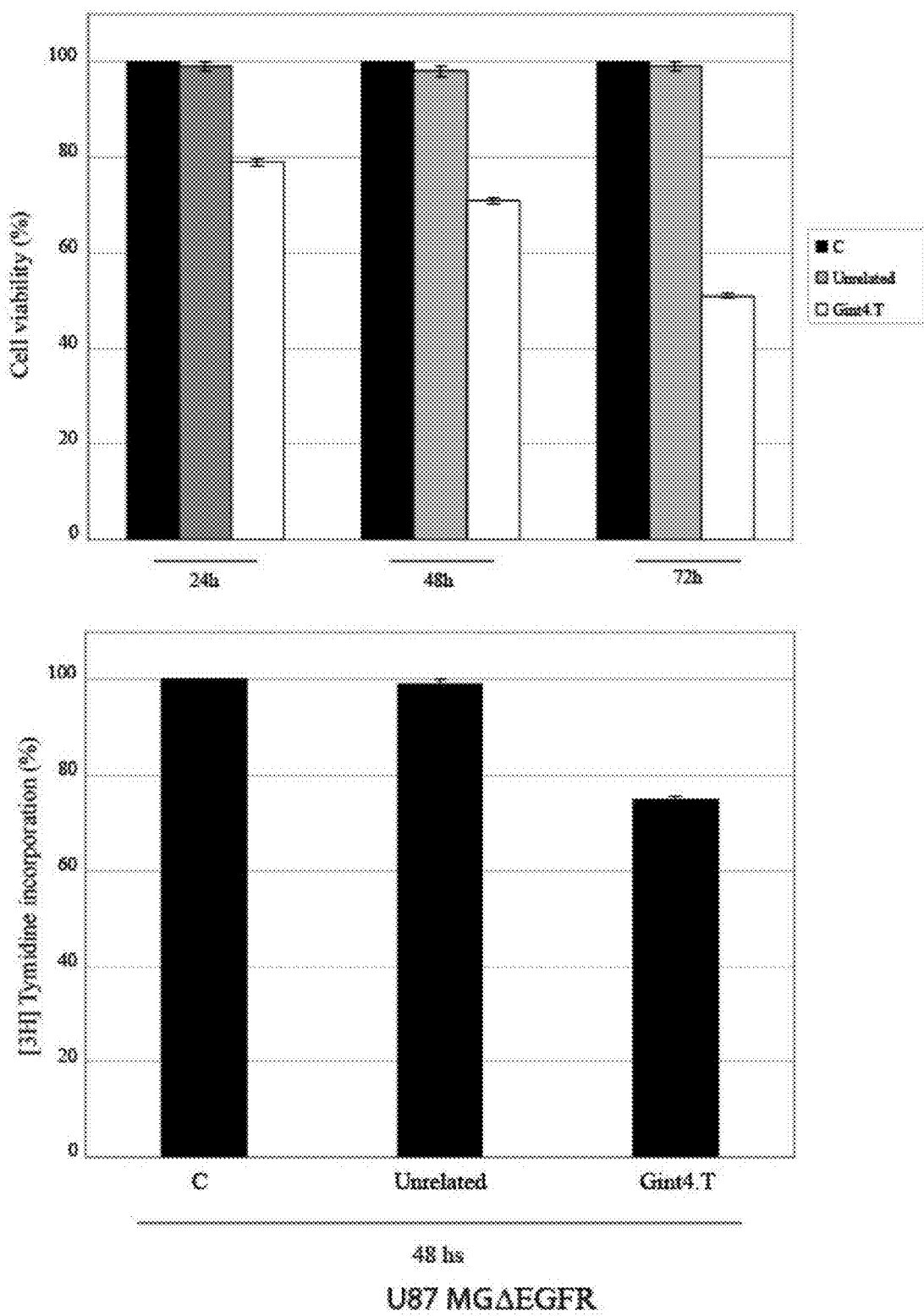
FIG. 6 shows that Gint4.T inhibits cell survival and proliferation.

FIG. 6. Gint4.T inhibits cell survival and proliferation. (Left panel) U87MGΔEGFR cells were left untreated or treated for 24, 48 and 72 hours with Gint4.T or the unrelated aptamer (200 nM-final concentration). Cell viability was analyzed as reported in Methods and was expressed as percent of viable treated cells with respect to control untreated cells (indicated with "C"). Error bars depict means±s.d. (n=4). (Right panel) U87MGΔEGFR cells were treated for 48 hours with Gint4.T or the unrelated aptamer (200 nM-final concentration) and proliferation was determined by [3H]-thymidine incorporation. Vertical bars indicate the standard deviation values.

Figure 7A:
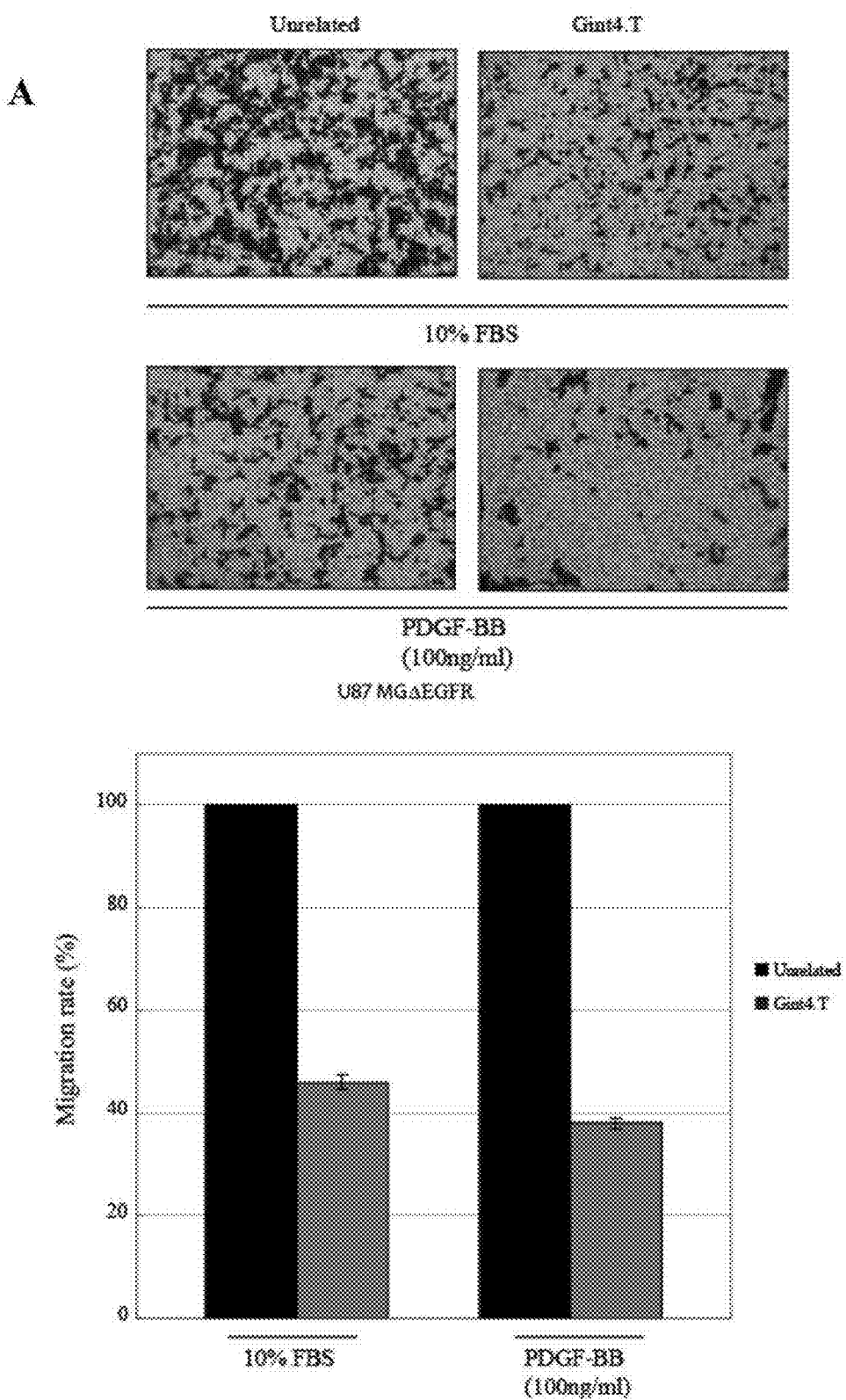
FIGS. 7A, 7B show that Gint4.T inhibits U87MGΔEGFR cell migration.
Figure 7B:
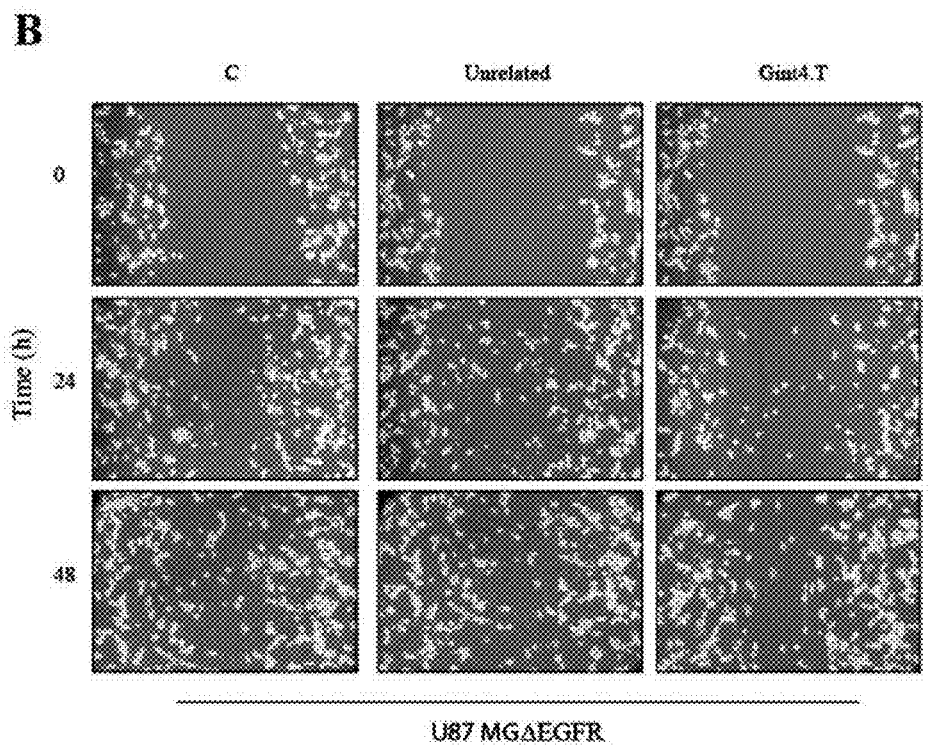
Figure 7B:
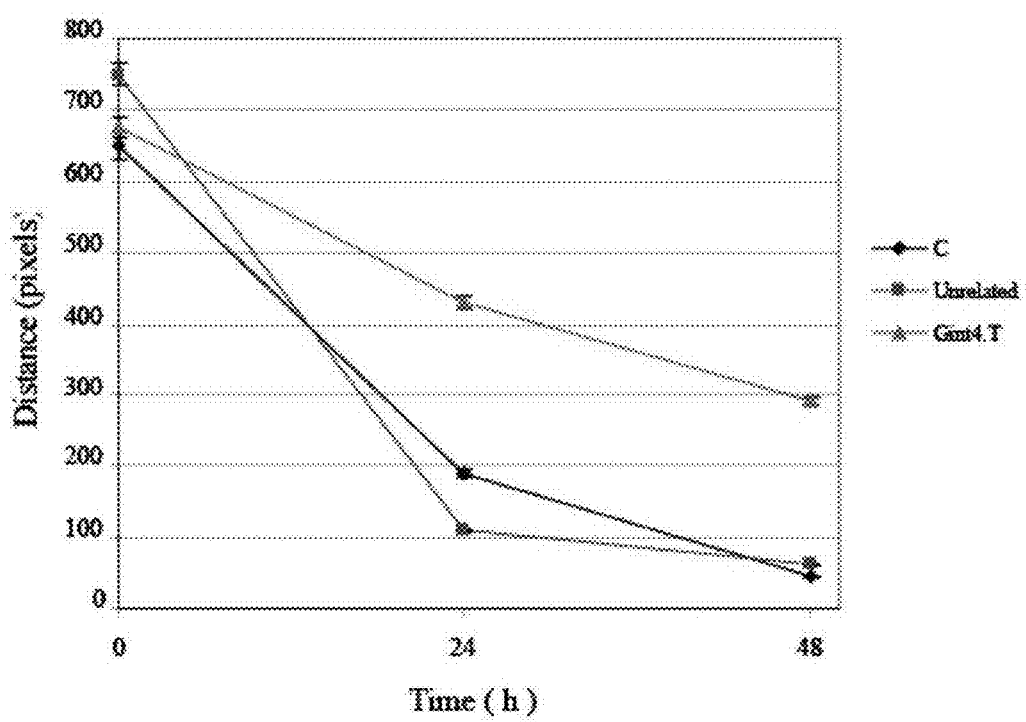

FIGS. 7A, 7B. Gint4.T inhibits U87MGΔEGFR cell migration. Motility of U87MGΔEGFR cells was analyzed by Transwell Migration Assay (A) in the presence of Gint4.T or the unrelated aptamer for 24, 48 and 72 hours toward 10% FBS or PDGFBB as inducers of migration. The migrated cells were stained with crystal violet and photographed. Representative photographs of at least three different experiments were shown. The results are expressed as percent of migrated cells in the presence of Gint4.T with respect to cells treated with the unrelated aptamer. Vertical bars indicate the standard deviation values. (B) Confluent monolayers of U87MGΔEGFR cells were subjected to scratch assays, as described in "Materials and methods" Section. Phase contrast microscopy images of untreated cells (indicated with "C") or treated with Gint4.T or the unrelated aptamer in the scratch assay at the beginning 0 and after 24 and 48 hours are shown. The cell migration distance was determined by measuring the width of the wound using ImageJ software for statistical analysis. Bars represent the mean±s.d. (n=3).

Figure 8A:
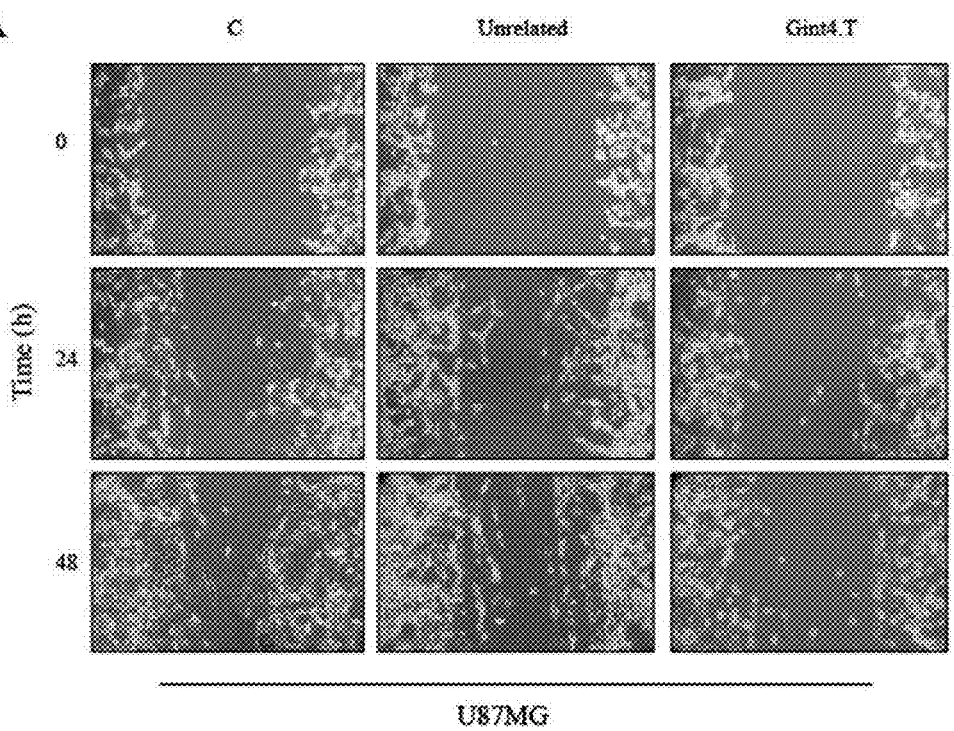
FIGS. 8A, 8B show that Gint4.T inhibits U87MG and T98G cell migration. Wound healing is demonstrated in U87MG (A) and T98G (B) cells.
Figure 8A:
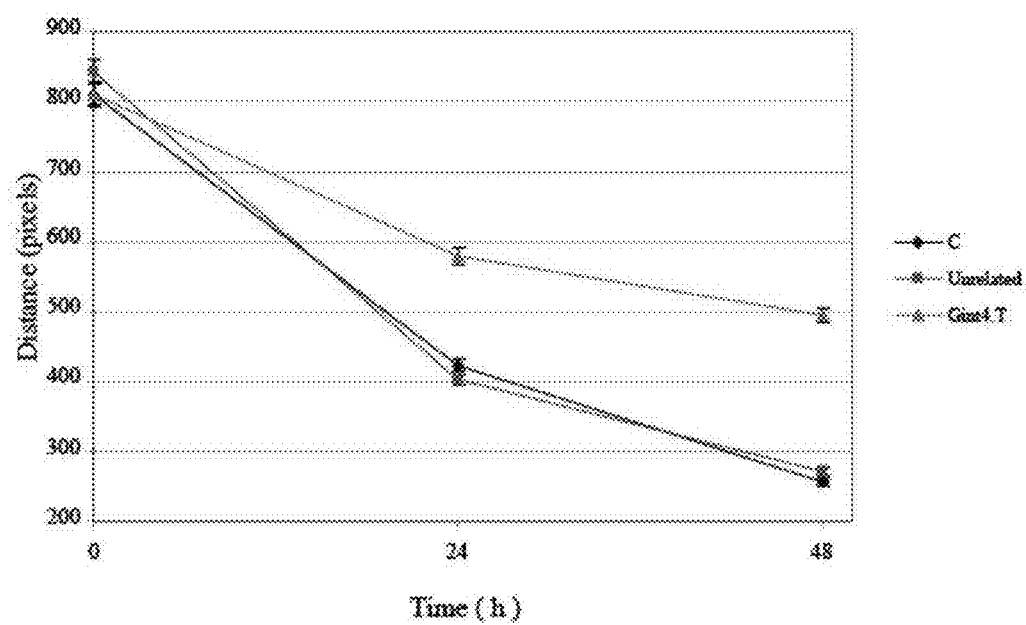
Figure 8B:
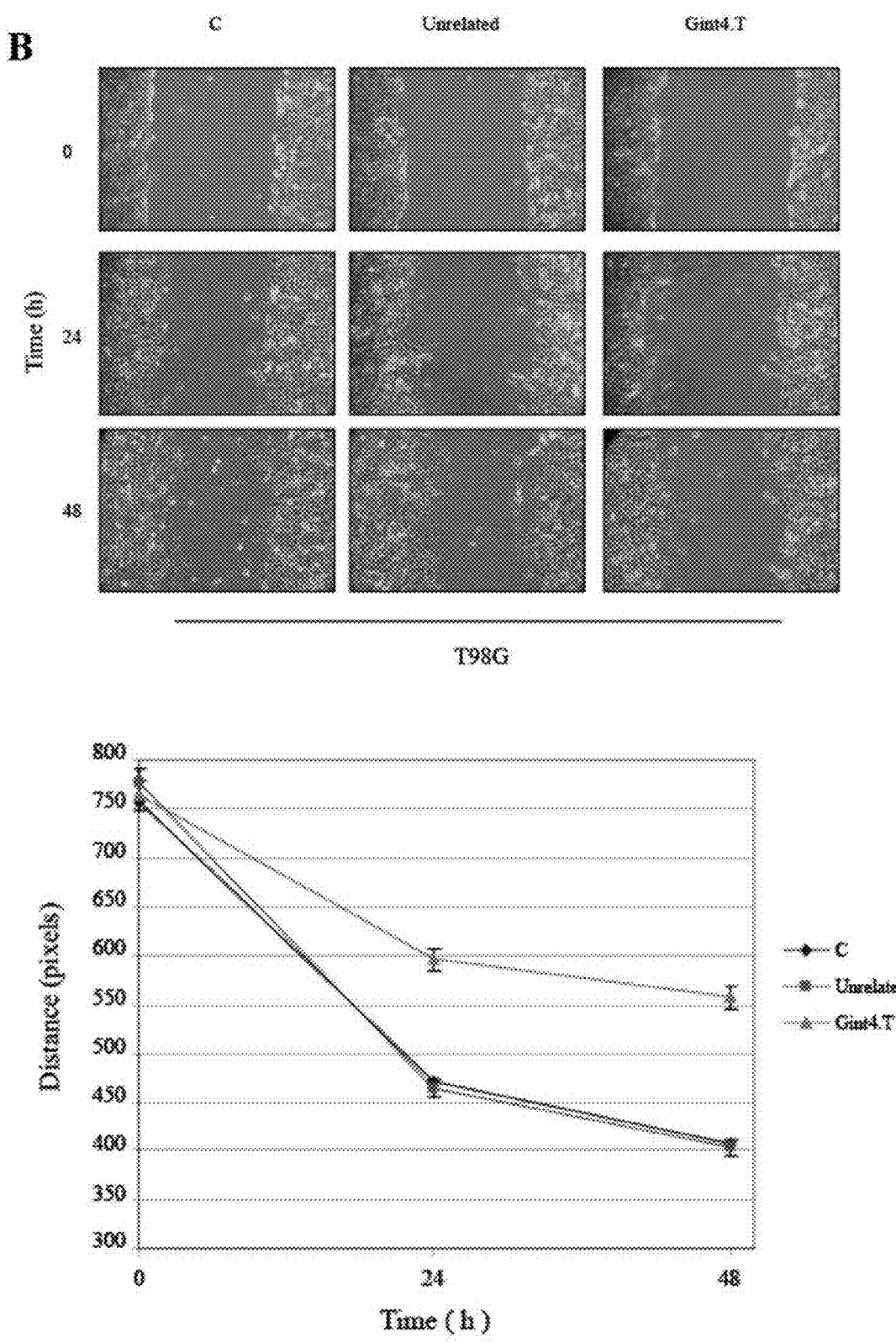

FIGS. 8A, 8B. Gint4.T inhibits U87MG and T98G cell migration. Wound healing in U87MG (A) and T98G (B) cells. The assays were carried out as described in the legend of FIG. 7B.

EXPERIMENTAL SECTION

1. Materials and Methods

Aptamers

Gint4.T and the unrelated 2'-fluoropyrimidine (2'F-Py) aptamer used as a negative control were purchased from TriLink.

```
Gint4.T aptamer:
5' UGUCGUGGGGCAUCGAGUAAAUGCAAUUCGACA 3'.

Unrelated aptamer:
5'UUCGUACCGGGUAGGUUGGCUUGCACAUAGAACGUGUCA3'.
```

Before each treatment, the aptamers were subjected to a short denaturation-renaturation step (85° C. for 5 min, snap-cooled on ice for 2 min, and allowed to warm up to 37° C.).

Cells

Human U87MG and T98G (American Type Culture Collection, Manassas, Va.) were grown in Dulbecco's modified Eagle medium (DMEM) supplemented with 2 mM L-glutamine, 10% fetal bovine serum (FBS) (Invitrogen, Carlsbad, Calif.). U87MGΔEGFR, expressing a truncated mutant EGFR receptor due to an in-frame deletion of exons 2-7 from the extracellular domain (ΔEGFR), were grown in DMEM supplemented with 2 mM L-glutamine, 10% fetal bovine serum, 500 mg/ml gentamycin (Invitrogen, Carlsbad, Calif.).

Binding Assays

Binding experiments were performed with 5'-[$^{32}$P]-labeled RNA. For labeling 2'-F-Py RNAs were 5'-end dephosphorylated using bacterial alcaline phosphatase (Invitrogen, Carlsbad, Calif.) before [$^{32}$P]-5'-end-labeled using T4 kinase (Invitrogen) and γ-[$^{32}$P]-ATP (6×10$^3$Ci/mmol, GE Healthcare Bio-Sciences, Uppsala, Sweden) according to the supplier's instructions.

For binding experiments on cells, 3.5×10$^4$ cells were plated in 24-well plates in triplicate and were incubated with Gint4.T aptamer and the unrelated sequence used as a negative control at 100 nM concentration in 200 μl of DMEM serum free for 20 min at RT in the presence of 100 μg/ml poly-inosine as a nonspecific competitor (Sigma, St. Louis, Mo.). After five washings with 500 μl DMEM, bound sequences were recovered in 300 μl of SDS 1%, and the amount of radioactivity recovered was counted.

The aptamers ability to bind PDGFRβ and PDGFRα soluble extracellular domain (EC-PDGFRβ and EC-PDGFRα, respectively; R&D Systems, Minneapolis, Minn.) was investigated by filter binding by incubating 1 nM of radiolabeled aptamers with 1, 3.2, 10, 32, 100, 320 and 1000 nM of EC-PDGFRβ and EC-PDGFRα as described.

In all binding assays the background values obtained with the unrelated aptamer were subtracted from the values obtained with the Gint4.T.

Internalization Assays

To check the endocytosis rate, 100 nM radiolabeled Gint4.T or unrelated aptamer have been incubated on U87MG cells for increasing incubation times (from 15 min up to 2 h) and at desired times, cells have been treated with 0.5 μg/μl proteinase K (Roche Diagnostics, Indianapolis, Ind., USA) at 37° C. Following 30-min treatment, the amount of RNA internalised has been recovered and counted.

Immunoblot Analyses

To assess the effects of aptamers on PDGFRβ activity, U87MG cells (1.5×10$^5$ cells per 3.5-cm plate) were serum-starved overnight, pretreated with 200 nM Gint4.T aptamer or the unrelated aptamer for 3 h and then stimulated for 5 min with 100 ng/ml PDGFBB (R&D Systems, Minneapolis, Minn.) either alone or in presence of each aptamer.

To prepare cell extracts, cells were washed twice in ice-cold PBS, and lysed in buffer A (50 mM Tris-HCl pH 8.0 buffer containing 150 mM NaCl, 1% Nonidet P-40, 2 mg/ml aprotinin, 1 mg/ml pepstatin, 2 mg/ml leupeptin, 1 mM Na$_3$VO$_4$). Protein concentration was determined by the Bradford assay using bovine serum albumin as the standard. The cell lysates were subjected to SDS-PAGE. Gels were electroblotted into polyvinylidene difluoride membranes (Millipore Co., Bedford, Mass.), and filters were probed with the indicated primary antibodies: anti-PDGFRβ, anti-phospho-PDGFRβ(Tyr771), anti-phospho-44/42 MAP kinase (E10) (also indicated as p-Erk), anti-phospho-AKT (Ser473), anti-AKT (Cell Signaling, Beverly, Mass., United States); anti-ERK1 (C-16) (Santa Cruz Biotechnology); anti-αtubulin (DM 1A) (Sigma, St. Louis, Mo.).

Proteins were visualized with peroxidase-conjugated secondary antibodies using the enhanced chemiluminescence system (GE Healthcare Bio-Sciences, Uppsala, Sweden). Where indicated, filters were stripped in 62.5 mM Tris-HCl pH 6.8 with 100 mM 2-mercaptoethanol and 2% SDS for 30 min at 54° C., and reprobed.

Cell Viability and [3H]-Thymidine Incorporation Assays

Cell viability was assessed with CellTiter 96 AQueous One Solution Cell Proliferation Assay (Promega, Madison, Wis.) according to the supplier's instructions (4×10$^3$ cells/well in 96-well plates). For cell proliferation assay, U87MGΔEGFR cells (2×10$^4$ cells/well in 24-well plates) were left untreated or treated for 48 hours with Gint4.T or unrelated aptamer. During the final 6 hours, cells were pulsed with 1 μCi/ml [3H]-thymidine (45 Ci/mmol) (Amersham Bioscience, Piscataway, N.J.) added in complete growth medium and incubated at 37° C. At the end of each pulse, cells were harvested and [3H]-thymidine incorporation was analyzed by a Beckman LS 1701 Liquid Scintillation Counter.

Transwell Migration Assay

U87MGΔEGFR cells were pretreated for 3 hours either with 200 nM Gint4.T or with unrelated aptamer and then trypsinized, re-suspended in DMEM serum free, and counted. Cells (1×10$^5$ in 100 μl serum-free medium per well) were then plated into the upper chamber of a 24-well transwell (Corning Incorporate, Corning, N.Y.) in the presence of either Gint4.T or unrelated aptamer (200 nM final concentration) and exposed to PDGFBB (100 ng/ml) or 10% FBS as inducers of migration (0.6 ml, lower chamber). After incubation at 37° C. in humidified 5% CO2 for 24 hours, cells were visualized by staining with 0.1% crystal violet in 25% methanol. Percentage of migrated cells was evaluated by eluting crystal violet with 1% sodium dodecyl sulfate and reading the absorbance at 570 nm wavelength.

Wound Healing Assay

U87MGΔEGFR, U87MG and T98G cells were plated in 6-well plates and grown to confluence. After serum starvation overnight in the absence or in the presence of 200 nM Gint4.T or the unrelated aptamer, cells were scraped to induce a "wound." Culture medium with 0.5% FBS with/without treatment with aptamers (200 nM-final concentration) was added and the wounds were observed using phase contrast microscopy. Images were taken at 0, 24 and 48 hours of both areas flanking the intersections of the wound and the marker lines (10 images per treatment). The cell migration distance was determined by measuring the width of the wound using ImageJ software for statistical analysis.

2. Results and Discussion

Identification of a RNA-Aptamer Actively Internalizing into Malignant Glioma Cells The aptamer of the invention, named Gint4, is a 2'-fluoro-pyrimidine (2'F-Py), nuclease-resistant RNA consisting of 91 nt (FIG. 1A) and generated by a differential cell-SELEX approach on highly tumorigenic glioma cell lines. The adopted selection strategy was the same that allowed us to select RNA-aptamers as high specific and affinity ligands for highly tumorigenic U87MG glioma cell lines (Cerchia et al., 2009; European patent publication EP 2159286. Inventors: L Cerchia, V de Franciscis, G Condorell), but included two further rounds of proteinase K-based selection intended to enrich for aptamers able to rapidly internalize within the target cells.

By different approaches we demonstrated that the Gint4 aptamer is rapidly endocytosed in U87MG glioma cells, getting about 25% of cell internalization following 15 min-incubation and reached about 40% following 30 min of aptamer treatment (FIG. 1B). Its internalization ability has been compared to that of GL21.T, the high affinity ligand of AxlRTK, that readily internalized into U87MG cells (Cerchia et al., 2012; patent "AXL RECEPTOR TYROSINE KINASE APTAMER INHIBITOR FOR USE IN THERAPY" PCT/EP2011/067624. Inventors: V de Franciscis, L Cerchia).

The Gint4.T Aptamer Specifically Interacts with the Extracellular Domain of the PDGFRβ

Using a rational approach based on its predicted secondary structure (as determined by two different softwares, DNAsis software and RNA structure 4.5 software) we designed a 33mer truncated version of the 91mer original molecule, named Gint4.T, that contains the active site of Gint4 (FIG. 2A) and preserves high binding affinity to the U87MG cells (FIG. 2B) and ability to rapidly enter into target cells (FIG. 2C).

As a first attempt to identify the functional targets of Gint4.T we performed a phospho-receptor tyrosine kinase (RTK) array analysis that provided us with convincing evidence that the target(s) of Gint4.T may belong to the PDGFR family (FIG. 3).

Therefore, to definitely determine the target of Gint4.T we first performed a filter binding analysis with the soluble extracellular domain of human PDGFRα and PDGFRβ as targets (here indicated as EC-PDGFRα and EC-PDGFRβ, respectively), that revealed a strong affinity of Gint4.T for EC-PDGFRβ (Kd of 9.6 nM) and comparable to that of the entire Gint4 (Kd of 10.4 nM), whereas no saturable binding was detectable for EC-PDGFRα (FIG. 4A and not shown).

Further, we show that binding of Gint4.T to the U87MG cells was strongly competed by the recombinant EC-PDGFRβ but not by EC-PDGFRα (FIG. 4B), thus confirming that recognition of target cells is mediated by aptamer binding to the extracellular domain of PDGFRβ on the cell surface and that the aptamer is able to discriminate PDGFRβ from the structurally similar PDGFRα receptor.

Taken together, these results indicate bona fide that the Gint4.T aptamer specifically recognizes PDGFRβ either if expressed on the cell surface in its physiological context as well as the purified soluble extracellular domain of the receptor. Further, because of its ability to rapidly internalize within PDGFRβ-positive target cells it is a highly promising candidate as cargo for tissue specific internalization.

The Gint4.T Aptamer Inhibits the PDGFRβ-Mediated Signal Pathways

Figure 5D:
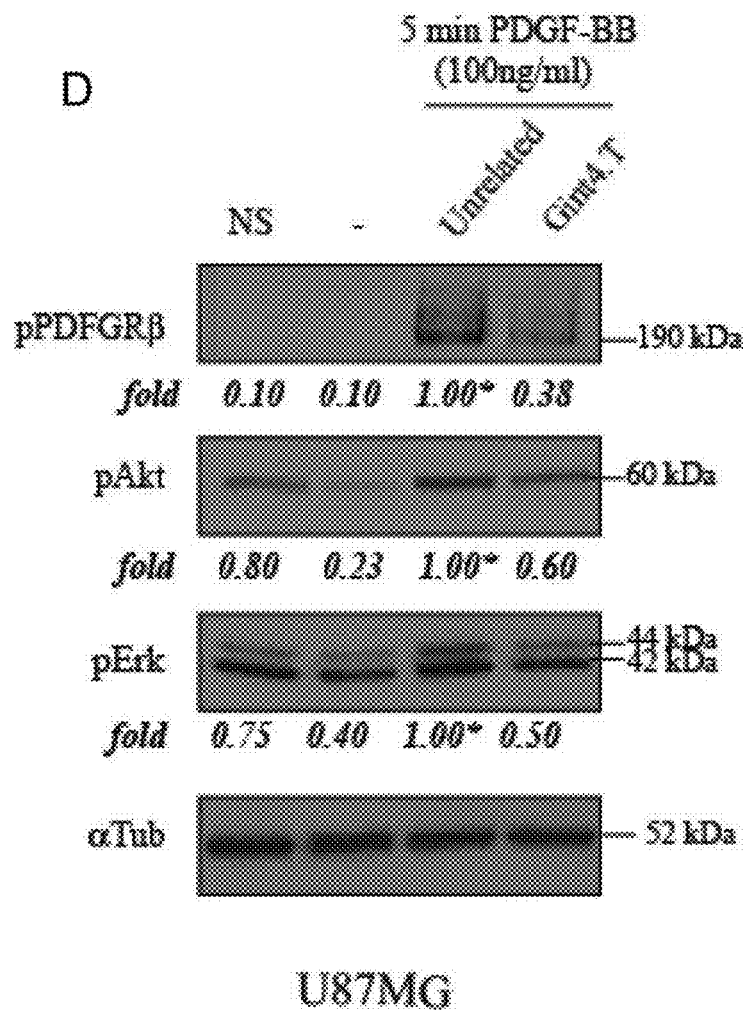

The treatment of PDGFRβ-positive U87MG cells with the aptamer strongly affects serum-induced PDGFRβ phosphorylation and activation of the intracellular pathways that are essential for cancer development and progression i.e. the ERK pathway involved in cell proliferation and the pro-survival Akt pathway (FIG. 5A). Further we demonstrated that the aptamer is as well able to block the PDGFBB-induced activation of the PDGFRβ receptor in U87MG (FIG. 5B) as well as in U87MGΔEGFR (FIG. 5C), a cell line expressing a truncated mutant EGFR receptor due to an in-frame deletion of exons 2-7 from the extracellular domain (ΔEGFR). In this cell line, it has been shown that the expression of ΔEGFR leads to activation of several cell surface RTKs including PDGFRβ (Pillay et al, 2009). Gint4.T treatment drastically reduced the tyrosine-phosphorylation of PDGFRβ causing about 70% inhibition at 5 min of PDGFBB treatment in both the cell lines, whereas no effect was observed in the presence of unrelated sequence used as a negative control. In addition, treating either U87MG (FIG. 5D) or U87MGΔEGFR (not shown) cells with Gint4.T drastically reduced the extent of PDGFBB-dependent activation of Erk and Akt. Erk1/2 and the PKB/Akt are intracellular signaling effectors that promote cell survival and proliferation. Therefore, because of Gint4.T inhibitory potential on the activation of both these pathways we determined whether the aptamer may reduce cell viability and proliferation in vitro. As assessed by MTT assay, interfering with PDGFRβ function reduced the percent of viable U87MGΔEGFR in a time dependent manner, reaching 50% following 72 hours of treatment (FIG. 6, upper panel). Consistently with the effects of Gint4.T on cell viability, treating U87MGΔEGFR cells with the aptamer for 48 h reduces [3H]-thymidine incorporation (FIG. 6, lower panel).

The Gint4.T Aptamer Inhibits Cell Migration

Intracellular signaling initiated by PDGFRβ has been reported to be mostly involved in cancer cell migration. To determine whether Gint4.T affects glioma cell migration, we used the Transwell migration assay and the wound healing assay. As shown in FIG. 7A treating U87MGΔEGFR cells with Gint4.T aptamer (200 nM final concentration) strongly reduces cell migration either stimulated by 10% fetal bovine serum (FBS) (upper panel) or by the PDGFBB ligand (lower panel) compared to the unrelated aptamer.

In addition, confluent monolayers of U87MGΔEGFR were scratched and images were taken at 0, 24 and 48 hours after wounding (FIG. 7B). The wound closure was significantly decreased in the presence of Gint4.T treatment compared to controls.

Further, in agreement with its ability to bind PDGFRβ-positive U87MG and T98G glioma cells, Gint4.T strongly reduced the wound closure of these cells in a time-dependent manner (FIG. 8A, 8B).

REFERENCES

Andrae J, Gallini R, Betsholtz C (2008). Role of platelet-derived growth factors in physiology and medicine. Genes Dev. 22:1276-312.

Betsholtz C, Karlsson L, Lindahl P (2001). Developmental roles of platelet-derived growth factors. Bioessays 23:494-507.

Cao R, Björndahl M A, Religa P, Clasper S, Garvin S, Galter D, Meister B, Ikomi F, Tritsaris K, Dissing S, Ohhashi T, Jackson D G, Cao Y (2004). PDGF-BB induces intratumoral lymphangiogenesis and promotes lymphatic metastasis. Cancer Cell. 6:333-45.

Cerchia L, de Franciscis V (2010). Targeting cancer cells with nucleic acid aptamers. Trends in Biotechnology 28:517-25.

Cerchia L, Esposito C L, Jacobs A H, Tavitian B, de Franciscis V (2009). Differential SELEX in human glioma cell lines. PLoS One 4:e7971 Cerchia L, Esposito C L, Camorani S, Rienzo A, Stasio L, Insabato L, Affuso A, de Franciscis V (2012). Targeting Axl with an high affinity inhibitory aptamer., Mol Ther. doi: 10.1038/mt.2012.163.

Cerchia L, Hamm J, Libri D, Tavitian B, de Franciscis V (2002). Nucleic acid aptamers in cancer medicine. FEBS Letters 528:12-6.

George D (2003). Targeting PDGF receptors in cancer—rationales and proof of concept clinical trials. Advances in Experimental Medicine and Biology 532:141-51.

Gilbertson R J, Clifford S C (2003). PDGFRB is overexpressed in metastatic medulloblastoma. Nature Genetics 35:197-8.

Hoch R V, Soriano P (2003). Roles of PDGF in animal development. Development 130:4769-84.

Andrae J, Gallini R, r Betsholtz C (2008). Role of platelet-derived growth factors in physiology and medicine. Genes Dev. 22: 1276-1312.

Kilic T, Alberta J A, Zdunek P R, Acar M, Iannarelli P, O'Reilly T, Buchdunger E, Black P M, Stiles C D (2000). Intracranial inhibition of platelet-derived growth factor-mediated glioblastoma cell growth by an orally active kinase inhibitor of the 2-phenylaminopyrimidine class. Cancer Research 60:5143-50.

Matsui T, Heidaran M, Miki T, Popescu N, La Rochelle W, Kraus M, Pierce J, Aaronson S (1989). Isolation of a novel receptor cDNA establishes the existence of two PDGF receptor genes. Science 243:800-4.

Pillay V, Allaf L, Wilding A L, Donoghue J F, Court N W, Greenall S A, Scott A M, and Johns T G (2009). The Plasticity of Oncogene Addiction: Implications for Targeted Therapies Directed to Receptor Tyrosine Kinases. Neoplasia 11(5): 448-458.

Shamah S M, Stiles C D, Guha A (1993). Dominant-negative mutants of platelet-derived growth factor revert the transformed phenotype of human astrocytoma cells. Molecular and Cellular Biology 13:7203-12

Ustach C V, Huang W, Conley-LaComb M K, Lin C Y, Che M, Abrams J, Kim H R (2010). A novel signaling axis of matriptase/PDGF-D/β-PDGFR in human prostate cancer. Cancer Res. 70:9631-40.

Vassbotn F S, Andersson M, Westermark B, Heldin C H, Ostman A (1993). Reversion of autocrine transformation by a dominant negative platelet-derived growth factor mutant. Molecular and Cellular Biology 13:4066-76.

Yarden Y, Escobedo J A, Kuang W J, Yang-Feng T L, Daniel T O, Tremble P M, Chen E Y, Ando M E, Harkins R N, Francke U, et al. (1986). Structure of the receptor for platelet-derived growth factor helps define a family of closely related growth factor receptors. Nature 323:226-32.

Yu J, Ustach C, Kim H R (2003). Platelet-derived growth factor signaling and human cancer. Journal of Biochemistry and Molecular Biology 36:49-59.

European patent application EP2436391 to ARCHEMIX LLC

European patent application EP2159286 to CONSIGLIO NAZIONALE DELLE RICERCHE (CNR)

The invention claimed is:

1. An RNA aptamer which comprises the nucleotide sequence 5' UGUCGUGGGGCAUCGAGUAAAUGCAAUUCGACA 3' (SEQ ID NO:1).

2. The RNA aptamer of claim 1, which consists of the nucleotide sequence 5' UGUCGUGGGGCAUCGAGUAAAUGCAAUUCGACA 3' (SEQ ID NO:1).

3. The RNA aptamer of claim 1, which consists of the nucleotide sequence GGGAGACAAGAAUAAACGCUCAAUCAUAAGAGGUAUCACAUUGUCGUGGGGCAUCGAGUAAAUGCAAUUCGACAGGAGGCUCACAACAGGC (SEQ ID NO:2).

4. The RNA aptamer of claim 1, wherein said aptamer is nuclease-resistant.

5. The RNA aptamer of claim 1, wherein at least one of the pyrimidine residues of the nucleotide sequence SEQ ID NO:1 or SEQ ID NO:2 is modified to 2'-fluoropyrimidine.

6. The RNA aptamer of claim 5, wherein all of the pyrimidine residues are modified to 2'-fluoropyrimidine.

7. The RNA aptamer of claim 1 for use in a diagnostic and/or therapeutic method.

8. The RNA aptamer of claim 7 for use in the diagnosis and/or therapy of a hyperproliferative disease.

9. The RNA aptamer of claim 8, wherein the hyperproliferative disease is selected from cancer and primary tumour metastasis.

10. The RNA aptamer of claim 9, wherein the hyperproliferative disease is selected from the group consisting of: gastrointestinal cancer, prostate cancer, ovarian cancer, breast cancer, head and neck cancer, lung cancer, non-small cell lung cancer, cancer of the nervous system (i.e. glioma), kidney cancer, retina cancer, skin cancer, liver cancer, pancreatic cancer, genital-urinary cancer, bladder cancer and metastatic cancers of any of the foregoing.

11. A pharmaceutical composition comprising the RNA aptamer of claim 1.

12. A kit for the diagnosis of a hyperproliferative disease comprising the RNA aptamer of claim 1.

\* \* \* \* \*